US012754158B2

(12) United States Patent
Sun et al.

(10) Patent No.: US 12,754,158 B2
(45) Date of Patent: Oct. 6, 2026

(54) SINGLE-CELL-BASED ELECTROCHEMICAL SENSOR BASED ON FUNCTIONALIZED NANO-PROBE AND APPLICATION THEREOF

(71) Applicant: Jiangnan University, Wuxi (CN)

(72) Inventors: Xiulan Sun, Wuxi (CN); Yongli Ye, Wuxi (CN); Jiadi Sun, Wuxi (CN); Liping Wang, Wuxi (CN); Jian Ji, Wuxi (CN); Yinzhi Zhang, Wuxi (CN); Lu Gao, Wuxi (CN)

(73) Assignee: Jiangnan University, Wuxi (CN)

( * ) Notice: Subject to any disclaimer, the term of this patent is extended or adjusted under 35 U.S.C. 154(b) by 1148 days.

(21) Appl. No.: 17/841,741

(22) Filed: Jun. 16, 2022

(65) Prior Publication Data

US 2022/0308005 A1 Sep. 29, 2022

Related U.S. Application Data

(63) Continuation of application No. PCT/CN2020/137569, filed on Dec. 18, 2020.

(30) Foreign Application Priority Data

Dec. 11, 2020 (CN) ........................ 202011459921.6

(51) Int. Cl.
*G01N 27/327* (2006.01)
*B82Y 15/00* (2011.01)
(Continued)

(52) U.S. Cl.
CPC ....... *G01N 27/327* (2013.01); *G01N 27/4161* (2013.01); *G01N 33/5014* (2013.01); *B82Y 15/00* (2013.01)

(58) Field of Classification Search
CPC ............ G01N 27/327; G01N 27/4161; G01N 33/5014; G01N 27/30; G01N 27/26; G01N 27/3278; B82Y 15/00
See application file for complete search history.

(56) References Cited

U.S. PATENT DOCUMENTS

2016/0356739 A1* 12/2016 Abdolahad .......... G01N 27/283

FOREIGN PATENT DOCUMENTS

CN 102262122 A 11/2011
CN 103105353 A 5/2013
(Continued)

OTHER PUBLICATIONS

Zhong et al., "A novel sandwich aptasensor for detecting T-2 toxin based on rGO-TEPA-Au@Pt nanorods with a dual signal amplification strategy," 2019, Biosensors and Bioelectronics, vol. 144, pp. 1-8 (Year: 2019).*
(Continued)

*Primary Examiner* — Benjamin L Utech
(74) *Attorney, Agent, or Firm* — IPro, PLLC; Na Xu

(57) ABSTRACT

The disclosure provides a single-cell-based electrochemical sensor based on a functionalized nano-probe and an application thereof, and belongs to the technical fields of electrochemical sensors and toxin detection. The single-cell-based electrochemical sensor of the disclosure combines a nano-probe and an electrochemical cell-based sensor, conducts functional modification on the nano-probe using Prussian blue, and conducts current signal analysis on a single cell by a micro-operating platform. The disclosure constructs a reliable, easy to operate and highly repeatable single-cell-based electrochemical detection platform, and the current value is determined by electrochemical chronoamperometry to determine damage of a single cell stimulated by toxins, thereby quickly and effectively evaluating
(Continued)

the cytotoxicity of fungal toxins, and further enabling application of the fungal toxin toxicity in real-time monitoring and nano-environmental detection in living cells.

7 Claims, 9 Drawing Sheets

(51) Int. Cl.
*G01N 27/416* (2006.01)
*G01N 33/50* (2006.01)

(56) References Cited

FOREIGN PATENT DOCUMENTS

| | | | |
|---|---|---|---|
| CN | 103713028 | A | 4/2014 |
| CN | 108344783 | A | 7/2018 |
| CN | 110057877 | A | 7/2019 |
| CN | 110308188 | A | 10/2019 |

OTHER PUBLICATIONS

Dai et al., "T-2 toxin neurotoxicity: role of oxidative stress and mitochondrial dysfunction," 2019, Archives of Toxicology, vol. 93, pp. 3041-3056 (Year: 2019).*

Liu et al., "Fabrication of single Pt@Au nanowire electrodes for monitoring hydrogen peroxide released from living cells," 2017, RSC Advances, vol. 7, pp. 44552-44558 (Year: 2017).*

Zhang et al., "Size-Dependent and Self-Catalytic Gold@Prussian Blue Nanoparticles for the Electrochemical Detection of Hydrogen Peroxide," 2020, ChemElectroChem, vol. 7, Abstract (Year: 2020).*

Liu, Aoxue "Modulating Nanoparticle Translocation by Surface Chemistry of Gold Nanopores" China Excellent Doctoral and Master's Thesis Full-text Database (Master) Engineering Science and Technology vol. 2019-09-15, ISSN:1674-0246.

Zhong Hangtian et. al., "A novel sandwich aptasensor for detecting T-2 toxin based on rGO-TEPA-Au@Pt nanorods with a dual signal amplification strategy", Biosensors and Bioelectronics, V144, 11635, Aug. 2, 2019.

* cited by examiner

SINGLE-CELL-BASED ELECTROCHEMICAL SENSOR BASED ON FUNCTIONALIZED NANO-PROBE AND APPLICATION THEREOF

TECHNICAL FIELD

The disclosure relates to a single-cell-based electrochemical sensor based on a functionalized nano-probe and an application thereof, and belongs to the technical fields of electrochemical sensors and toxin detection.

BACKGROUND

Cell-based sensors can be used to qualitatively or quantitatively detect unknown toxic substances, and determine the presence and content of such substances based on specific properties of excitatory effect potentials and cellular mechanisms, thereby detecting and evaluating harmful substances. Research at the level of individual cells can obtain more accurate and comprehensive information reflecting the physiological state and process of cells, and enable us to better understand some special cell functions in cell populations, and learn more in-depth information such as intercellular differences, intercellular interaction information, and physiological effects of neurotransmitters and drug stimulation. Nanoelectrochemistry plays a key role in a wide range of interdisciplinary studies in biochemistry, neuroscience, catalysis, molecular electronics, nanoscience (such as nanopores, nanobubbles, and nanoparticles), polymer science, electrodeposition, renewable technologies, etc. Due to a small size, nanoelectrodes minimize damage during penetrating living cells, and are particularly favorable for intracellular measurement of such species. In recent years, with the development of nanoelectrochemistry, chemical measurement in solutions has nanometer spatial resolution, high temporal resolution, and ultra-high sensitivity and selectivity.

T-2 toxins are a fungal toxin produced by the genus Fusarium, belonging to class A trichothecenes, and having the highest toxicity. T-2 toxins exist widely in nature, and T-2 toxins may exist in field crops such as barley, wheat, oat, rye and corn, as well as in stocked grains. Moreover, T-2 toxins can be produced in a temperature range of −2° C. to 35° C., and the yield increases with environmental humidity. T-2 toxins are difficult to degrade, and are a serious threat to human and animal health because ordinary cooking methods cannot reduce their toxicity. In 1973, the Joint FAO/WHO Expert Committee on Food Additives (JECFA) identified T-2 toxins as one of the most dangerous natural food contamination toxins. In 2017, China issued a national standard for plant-based feed ingredients and compound feed for pigs and poultry, stipulating that T-2 toxins in feed should not exceed 0.5 mg/kg. T-2 toxins can induce oxidative stress reaction in a variety of cells in vivo and in vitro. Many researchers also explain many toxic effects caused by T-2 toxins from the perspective of oxidative stress, such as cytotoxicity, immunotoxicity, genotoxicity, reproductive toxicity and neurotoxicity. Hydrogen peroxide is the most representative free radical of intracellular reactive oxygen species (ROS), and the level of intracellular reactive oxygen species hydrogen peroxide is closely related to the physiology and pathology of organisms. However, overproduction of ROS can overwhelm cellular free radical scavenging and repair systems, leading to tissue dysfunction and oxidative stress. T-2 toxins can activate an ROS-dependent mitochondrial apoptosis pathway, thereby causing mitochondrial dysfunction.

The current toxicity assessment methods mainly rely on multicellular experiments and animal experiments. The multicellular experimental methods have low cost, short cycle and certain homology with a body, but multicellular culture has low sensitivity and cannot realize real-time monitoring. Although the results of animal toxicology experiments can truly, comprehensively and systematically reflect the effects of drugs on the body, animal toxicology experiments have disadvantages of high cost, long cycle, unsatisfactory repeatability, etc.

With the development and progress of science and technology, a variety of new technologies and new methods combining traditional cell technology and sensor technology provide more new means for the study of toxicity mechanism. In construction of a cell-based sensor, a cell is immobilized on an interface as a receptor. When stimulated by external drugs, the physiological activity of the cell will change, the changes can be converted into photoelectric signals, and the magnitude of signal changes can be used to qualitatively and quantitatively analyze the drug stimulation received by the cell. Patent (CN201610231154.0) provides a method for cell-based detection of saxitoxin, with a detection linear range of 1-10 nM, that is, 2.99-29.9 ppb, high detection limit, and low sensitivity. The method is combined with ELISA, and does not utilize an electrochemical sensing method. Patent (CN201310511626.4) discloses a graphene-based single-cell-based sensing method. Specifically, graphene is transferred to a transparent substrate, an appropriate microfluidic channel is selected according to the size of a cell to be tested and pasted on the graphene, a beam is focused and irradiated to the graphene covered with the microfluidic channel, the emergent light is divided into s and p polarizations and irradiated to two probes of a balanced detector respectively, a voltage signal is collected, and the cell signal is analyzed and processed to obtain characteristic information of the cell. However, the method can only distinguish single cell morphology, and needs further research for drug detection.

SUMMARY

To solve at least one of the above problems, the disclosure provides a single-cell-based electrochemical sensor based on a functionalized nano-probe and application thereof to T-2 fungal toxins. The disclosure combines a nano-probe and an electrochemical cell-based sensor to construct a reliable, easy to operate and highly repeatable hepatoma single-cell system, and the current value is determined by electrochemical chronoamperometry to determine damage of a single cell stimulated by toxins, thereby quickly and effectively evaluating cytotoxicity of fungal toxins.

The first objective of the disclosure is to provide a functionalized nano-probe for single-cell-based electrochemical sensing, and a construction method of the functionalized nano-probe includes the following processes: a capillary is pulled into a nano-microneedle, gold nanoparticles are deposited on a microneedle tip to prepare a nano-probe, and then Prussian blue is deposited on the nano-probe to obtain the functionalized nano-probe.

In an implementation of the disclosure, the process of depositing gold nanoparticles includes: the microneedle tip is immersed and deposited in a sulfuric acid solution containing chloroauric acid at an initial potential of −0.25 V for 15-20 s.

In an implementation of the disclosure, the concentration of chloroauric acid in the sulfuric acid solution is 1 mmol·$L^{-1}$, and the concentration of sulfuric acid is 0.5 mol·$L^{-1}$.

In an implementation of the disclosure, the process of Prussian blue deposition includes: electrochemical deposition is conducted in a plating solution containing 0.1 M of HCl, 2 mM of $FeCl_3$, 0.1 M of KCl, and 2 mM of $K_3[Fe(CN)_6]$, at a potential of 0.2 V to −0.6 V for 50 cycles.

In an implementation of the disclosure, the tip radius of the functionalized nano-probe is 200-400 nm.

In an implementation of the disclosure, the specific process of the nano-probe includes: the initially pulled tip opening is 200 nm; electroplating is conducted with gold nanoparticles of 50-100 nm, at an initial potential of −0.25 V for 20 s; and a 1-2 cm gold layer is exposed at the probe tip as an electrochemical sensing part.

In an implementation of the disclosure, a preparation method of the functionalized nano-probe specifically includes:

(1) a glass capillary is pulled into a nano-microneedle by a micropipette puller, the tip to be characterized is coated with gold nanoparticles by electrodeposition, the outer layer of an electrode is insulated with PDMS, the surface of the nano-probe is wrapped with Apiezon wax, and the gold layer is exposed at the tip as the electrochemical sensing part; and (2) the nano-probe is further modified with Prussian blue by electrochemical deposition, the potential is cycled for 50 times, and the Prussian blue-modified nano-probe is rinsed with deionized water and dried at room temperature.

The second objective of the disclosure is to provide a single-cell-based electrochemical sensor, including the above functionalized nano-probe as a working electrode.

The third objective of the disclosure is to provide a single-cell-based toxicity detection method using the above functionalized nano-probe.

The above functionalized nano-probe is clamped on a micro-operating system for automatic control, and is directly penetrated into a cell for electrochemical detection.

In an implementation of the disclosure, the single-cell-based electrochemical sensor conducts direct electrochemical detection of a single cell.

In an implementation of the disclosure, the cell is a human hepatoma cell HepG2.

In an implementation of the disclosure, the detection method is to localize the functionalized nano-probe on a single cell at a distance of 500 μm from other cells.

The fourth objective of the disclosure is to provide a method for detecting toxicity of Class A T-2 trichothecenes using the above single-cell-based electrochemical sensor, and the method includes: a toxin standard substance is diluted with an MEM cell culture medium into solutions with gradient concentrations, the solutions are added to a cell culture dish, electrochemical detection is conducted in 5 min, and the cytotoxicity of the toxins is analyzed by electrochemical chronoamperometry.

In an implementation of the disclosure, the process of analyzing the cytotoxicity of toxins by electrochemical chronoamperometry includes:

a standard curve A is constructed by using concentration values of $H_2O_2$ standard samples with different concentrations and current values output by the single-cell-based electrochemical sensor; then a standard curve B is constructed using concentration values of toxin standard samples with different concentrations and concentration values of $H_2O_2$; and by detecting current values of samples to be tested, based on the standard curves A and B, the concentrations of toxins in the samples to be tested are measured.

In an implementation of the disclosure, the single-cell-based sensor needs to conduct cell culture before application, and the specific operations are as follows: cells in a logarithmic growth phase are subcultured for 1:5, and incubated in an incubator of 37° C. with a carbon dioxide concentration of 5% and a humidity of 95% for 6-12 h; toxin standard substances are diluted with an MEM cell culture medium into solutions with gradient concentrations; and the solutions are added to culture dishes respectively and subjected to electrochemical detection 5 min later.

In an implementation of the disclosure, current signals are measured on an Autolab PGSTAT302N electrochemical workstation, and working signals are collected at 600 mV.

In an implementation of the disclosure, before the hydrogen peroxide detection, a standard curve of concentrations versus current values needs to be drawn for a hydrogen peroxide solution with a determined concentration.

In an implementation of the disclosure, the single-cell detection is conducted under an inverted microscope using the micro-operating system SenSapex UMP.

In an implementation of the disclosure, the T-2 toxin evaluation is the detection of reactive oxygen species, especially hydrogen peroxide, produced in cells.

The fifth objective of the disclosure is an application of the single-cell-based electrochemical sensor in the fields of drug development for non-disease diagnosis and treatment, toxicology testing, and nano-environment real-time monitoring.

Compared with the prior art, the disclosure has the following advantages:

(1) The disclosure uses the modified functionalized nano-probe specifically detecting hydrogen peroxide in cells, so that the prepared sensor has higher sensitivity and lower detection limit for toxin detection.

(2) A nano-electrode used in the disclosure can minimize damage in the process of penetrating living cells due to a small size, and can conduct measurement in a single cell and real-time signal detection of toxins.

(3) The single-cell-based sensor of the disclosure can evaluate the degree of toxicity of T-2 fungal toxins. For a long time, grains and feed are seriously polluted by fungal toxins in China. The disclosure can evaluate the cytotoxicity of a single toxin, further determine its mechanism type, and provide a reference for determination of relevant detection standards.

(4) The disclosure constructs a single-cell-based electrochemical detection system by rationally combining the functionalized nano-probe with single-cell-based electrochemical sensing. The method is convenient in operation, reliable and sensitive, provides a new method and new idea for evaluating a toxic nano-environment of fungal toxins, and is expected to be applied in the fields such as food safety and biomedicine.

DETAILED DESCRIPTION

The preferred examples of the disclosure will be described below, and it is appreciated that the examples are intended to better explain the disclosure rather than limit the disclosure.

The “capillary” and “glass capillary” involved in the disclosure are both capillaries pulled from indium tin oxide (ITO) conductive glass. ITO conductive glass is a transparent ITO film coated on a glass surface by magnetron sputtering. ITO conductive glass can be purchased from Xi’an Qiyue Biological Technology Co., Ltd.

Example 1 Preparation of Single-Cell-Based Electrochemical Sensor

Figure 1:
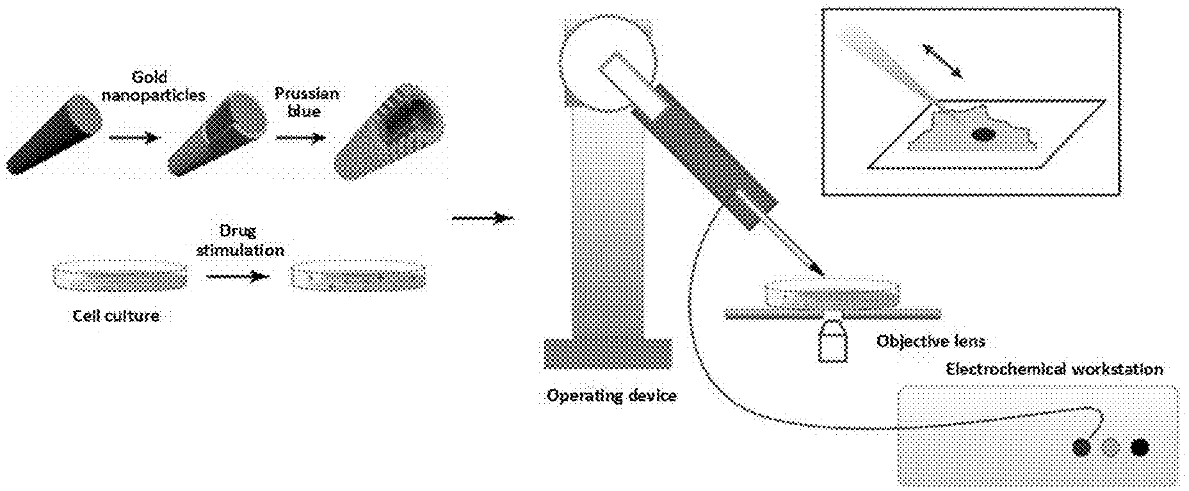
FIG. 1 shows a flow diagram of a single-cell-based electrochemical sensor based on a functionalized nano-probe in Example 1.

A method for constructing a single-cell-based electrochemical sensor based on a functionalized nano-probe (FIG. 1) includes the following steps:

(1) Cell culture: HepG2 human hepatoma cells were cultured in an MEM culture medium containing 10% of fetal bovine serum and 1% of penicillin-streptomycin (100 μg/mL) in a 37° C. incubator with a saturated humidity and 5% of $CO_2$. The cells grew adherently, and the culture medium was changed every 3 days. When the cells covered 90% of the bottom area of a flask, the cells were subcultured.

(2) Preparation of a nano-probe: A glass capillary was pulled into a nano-microneedle with a tip opening of about 200 nm by a micropipette puller. The tip to be characterized was coated with gold nanoparticles of about 50-100 nm by electrodeposition (the nano-probe was immersed in a 0.5 $mol \cdot L^{-1}$ sulfuric acid solution containing 1 $mmol \cdot L^{-1}$ chloroauric acid at an initial potential of −0.25 V for 20 seconds). The outer layer of the electrode was insulated with PDMS. The surface of the nano-probe was wrapped with Apiezon wax. A 1-2 cm Au layer was exposed at the tip as an electrochemical sensing part.

(3) Modification of a functionalized nano-probe: The nano-probe was further modified with Prussian blue (PB) by electrochemical deposition in a deposition solution containing 0.1 M of HCl, 2 mM of $FeCl_3$, 0.1 M of KCl, and 2 mM of $K_3[Fe(CN)_6]$. The potential was cycled in a range of 0.2 V to −0.6 V for 50 times. Then the PB-modified nano-probe was rinsed with deionized water and dried at room temperature.

Figure 2A:
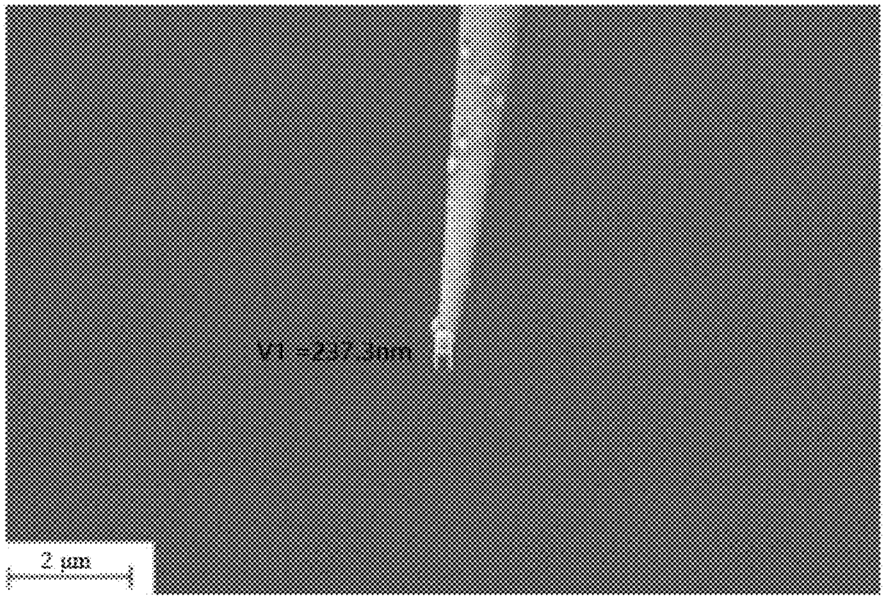
FIG. 2A is an electron microscope characterization diagram of the nano-electrode in Example 1.

The prepared functionalized nano-probe was characterized by scanning electron microscopy (FIG. 2A). The diameter of the nano-probe tip was in a range of 200-400 nm.

Figure 2B:
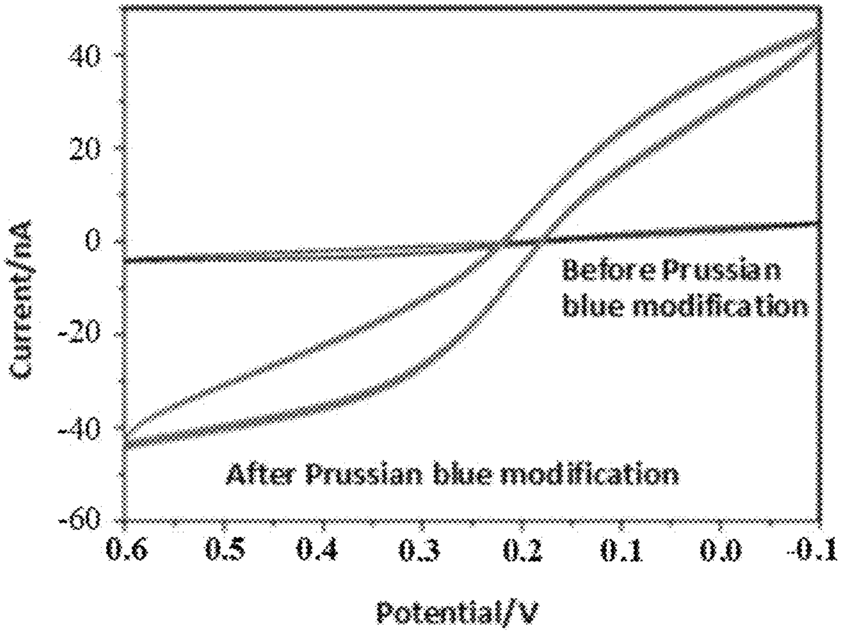
FIG. 2B shows electrochemical characterization before and after Prussian blue modification in Example 1.

Cyclic voltammogram characterization was tested using a CHI660e electrochemical workstation with a probe tip in an electrolyte containing 2.5 mM of $Fe(CN)_6^{3-/4-}$ and 1.0 M of KCl, the reference electrode and auxiliary electrode are an Ag electrode and a Pt electrode respectively, the cycle voltage is −0.1 V to 0.6 V, and the scanning speed is 0.1 V/s. Comparing redox signals before and after modification, FIG. 2B shows that a characteristic signal peak appeared at ~−0.1 V after PB modification, and the reduction peak responded to a conversion of PB to Prussian white (PW), and this was necessary for electrocatalysis of $H_2O_2$. As an electron transport medium, PW has a function of reducing $H_2O_2$, indicating that PB was successfully deposited on the nano-probe.

Figure 3:
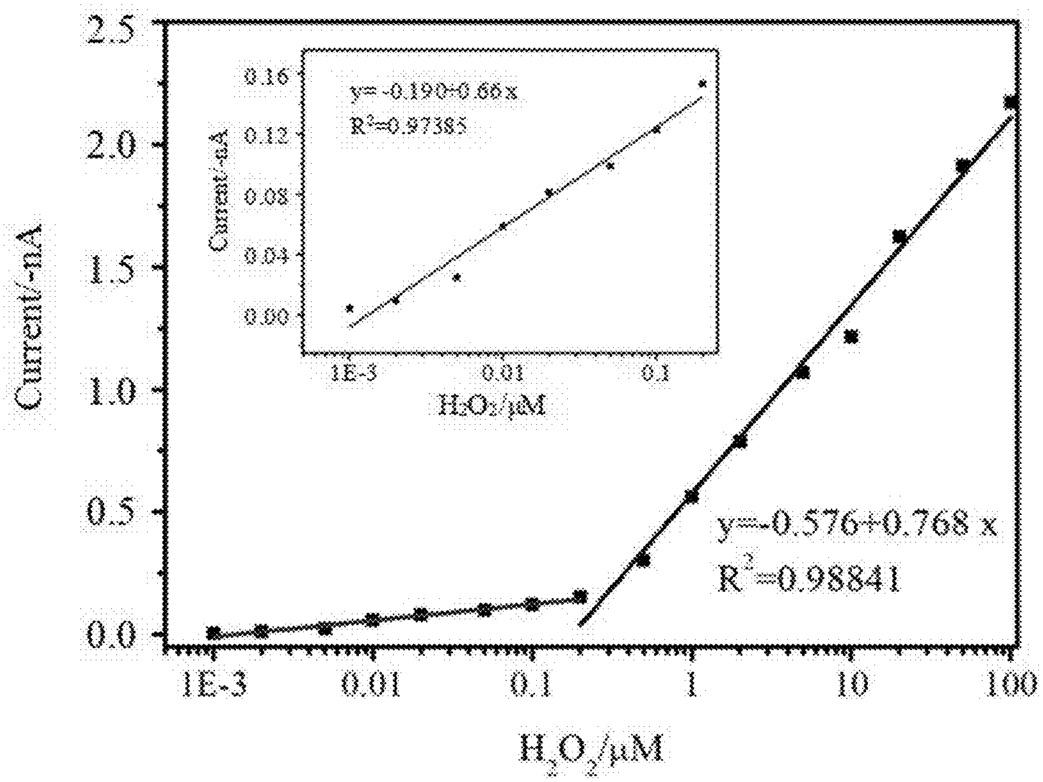
FIG. 3 shows a calibration chart of steady state currents versus $H_2O_2$ concentrations. The inset shows a linear relationship between $H_2O_2$ of 1 nM-100 nM and peak currents.

The nano-probe was used to collect current signals of $H_2O_2$ solutions with different concentrations at a voltage of 0.6 V. FIG. 3 shows the corresponding calibration curve. 0.1 μM-100 μM $H_2O_2$ is linear to current values, $R_1^2$=0.98841. The inset shows the linear relationship between 1 nM-100 nM $H_2O_2$ and electrical signals, $R_2^2$=0.97385.

Example 2 Application of Single-Cell-Based Electrochemical Sensor Based on Functionalized Nano-Probe The single-cell-based electrochemical sensor obtained in Example 1 was used to evaluate the single-cell toxicity of T-2 fungal toxins, as follows:

(1) Drug stimulation: The original culture medium in the culture dish was removed. A toxin standard substance was diluted with an MEM cell culture medium into solutions with gradient concentrations. Then 0 ppb, 1 ppb, 10 ppb, 100 ppb, and 1 ppm T-2 toxins were added to cell culture dishes, and subjected to single-cell-based electrochemical detection 5 min later.

(2) Detection of electrochemical signal values: Current signals were measured at room temperature by chronoamperometry on an Autolab PGSTAT302N electrochemical workstation, and working signals were collected at 600 mV. All electrochemical experiments were conducted using a traditional three-electrode system, with a working electrode positioned on a single cell and at least 500 μm away from other cells. Single-cell detection was conducted under an inverted microscope using a micro-operating system SenSapex UMP. The PB-modified gold nano-probe was penetrated into a HepG2 cell by the micro-operating system.

Using air as a blank control, a chronoamperogram of cells stimulated by T-2 toxins with different concentrations was recorded at a fixed potential of 600 mV (vs-Ag/AgCl). After blank subtraction, a current versus concentration diagram was drawn to obtain a linear graph and obtain a detection limit. A calculation equation of the detection limit is shown in (1):

$$LoD = \frac{3.33 \times SD}{\text{slope}} \tag{1}$$

where SD is the standard deviation of the lowest concentration, and slope is the fitting slope of the curve.

(3) Result Determination

Figure 4A:
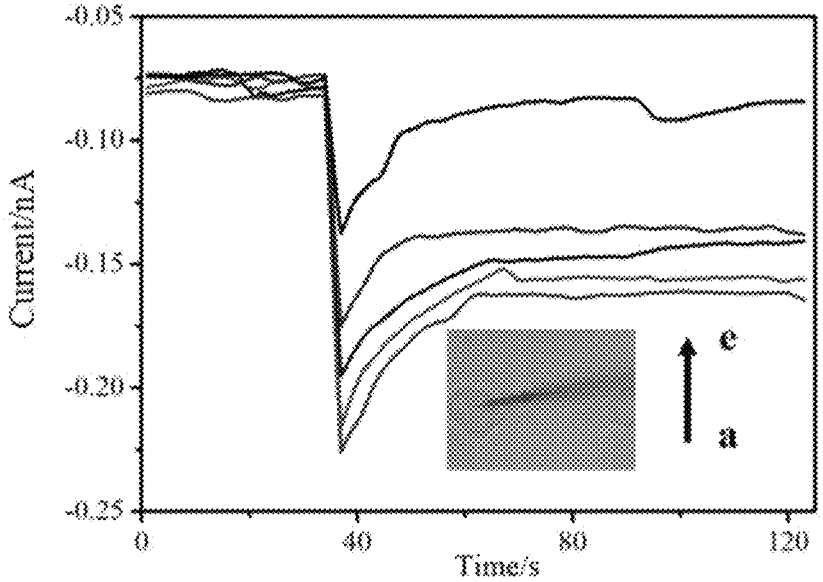
FIG. 4A shows detection results in evaluation of T-2 toxins by the single-cell-based electrochemical sensor in Example 2: a real-time chronoamperogram of cells stimulated by a. 1 ppb, b. 10 ppb, c. 100 ppb, d. 1 ppm, and e. 0 ppb (control group) T-2 toxin (the probe is penetrated into a single cell at 35 s), the inset is an optical micrograph of the nano-probe infiltrated into a single HepG2 cell.
Figure 4B:
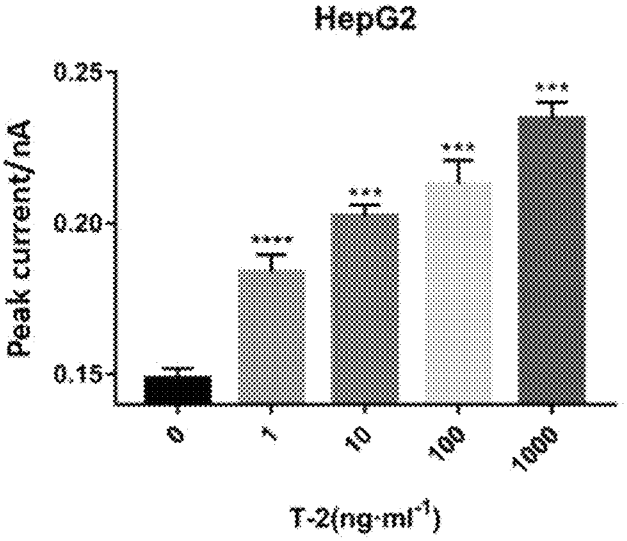
FIG. 4B shows the peak currents of T-2 toxins detected by the HepG2 single-cell-based sensor (n=4). $p<0.05$=*, $p<0.005$=, $p<0.001$=*, $p<0.0001$=****, and the same applies hereinafter.
Figure 4C:
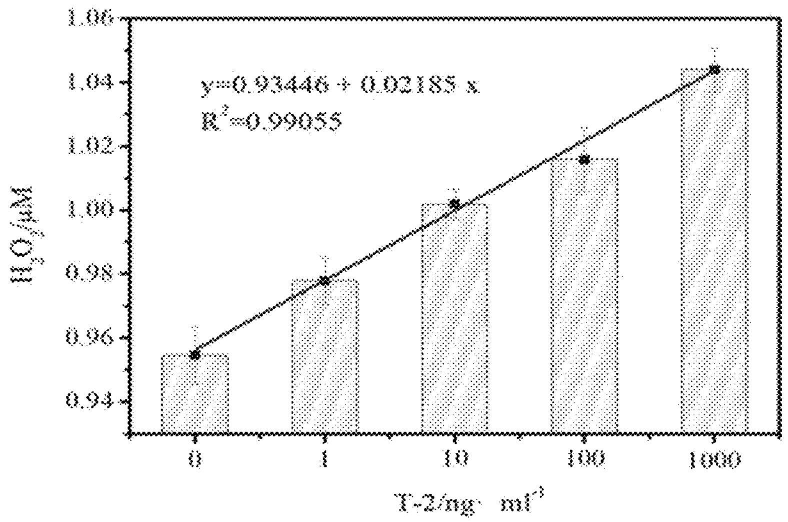
FIG. 4C shows the peak current values, of T-2 toxin-stimulated cells detected by single-cell-based electrochemical sensing, versus the $H_2O_2$ concentrations, and a linear fitting is conducted.

As shown in FIG. 4A, at 600 mV, a nano-probe was located away from the cell, then gradually approached and penetrated the cell at about 35 seconds. Different cathodic current peaks appeared in the cells stimulated with T-2 toxins of different concentrations. The peak current in a control cell was −0.14 nA, and the peak current in the cell stimulated with 1 ppm T-2 toxin reached −0.24 nA. FIG. 4B shows significant differences between each peak value and the control group. The higher the concentration of the T-2 toxin, the higher the peak current. This current signal indicated that under the stimulation of the T-2 toxin, HepG2 cells exhibited oxidative stress to varying degrees, produce $H_2O_2$ and prompt the probe to react, resulting in changes in electrochemical signals. T-2 toxin concentrations were corresponded to and linearly fitted with $H_2O_2$ concentrations (FIG. 4C), the $H_2O_2$ concentrations produced by $H_2O_2$ cells stimulated by T-2 toxins at 1 ppb-1 ppm were linearly correlated, $R^2$=0.99055, the detection limit was 0.13807 ng/mL, and the lowest detection concentration was 1 ng/mL.

(4) Sample Adding Standard Experiment

Sample addition experiments were conducted on flour and T-2 toxins with the concentrations of 0 ppb, 1 ppb, 10 ppb, 100 ppb, 1000 ppb were added (Table 1). The average adding standard recovery of samples based on single-cell electrochemical sensing was 81.19%-130.17%, indicating that the method has high accuracy and detection efficiency, and can be used for the detection of T-2 toxins in real samples.

TABLE 1

Sample adding standard recovery results

| T-2 toxin adding standard concentration ($ng \cdot mL^{-1}$) | Measured peak current (−nA) | T-2 toxin detection concentration ($ng \cdot mL^{-1}$) | Recovery (%) |
|---|---|---|---|
| 0 | 0.14428 | 0.0085 | — |
| 1 | 0.18265 | 1.1896 | 118.96 |
| 10 | 0.20125 | 13.01743 | 130.17 |
| 100 | 0.21649 | 92.4531 | 92.45 |
| 1000 | 0.23338 | 811.8900 | 81.19 |

Example 3 Verification Experiment

Detection of cytotoxicity induced by T-2 toxins by a CCK8 method: Human hepatoma cells HepG2 with a density of $5\times10^4$ cells/mL were adherently inoculated into a 96-well plate and cultured for 24 h, a culture medium was removed, and 100 μL of toxin solutions of the same doses as in Example 2 were added. After toxin stimulation for 24 h, the supernatant was pipetted, and 100 μL of a culture medium containing 10% CCK8 was added to each well for incubation at 37° C. for 2 h. Then the absorbance value was measured at 450 nm using a microplate reader, and the cell viability inhibition rate was calculated by an equation as follows:

$$\text{Inhibition rate (\%)} = \left(1 - \frac{OD_{dosed} - OD_{blank}}{OD_{0\ dosed} - OD_{blank}}\right) \times 100$$

wherein $OD_{dosed}$: Absorbance value after toxin stimulation for 24 h; $OD_{0\ dosed}$: Absorbance value without toxin stimulation in 24 h; and $OD_{blank}$: Absorbance value of a pure cell culture medium.

Figure 5:
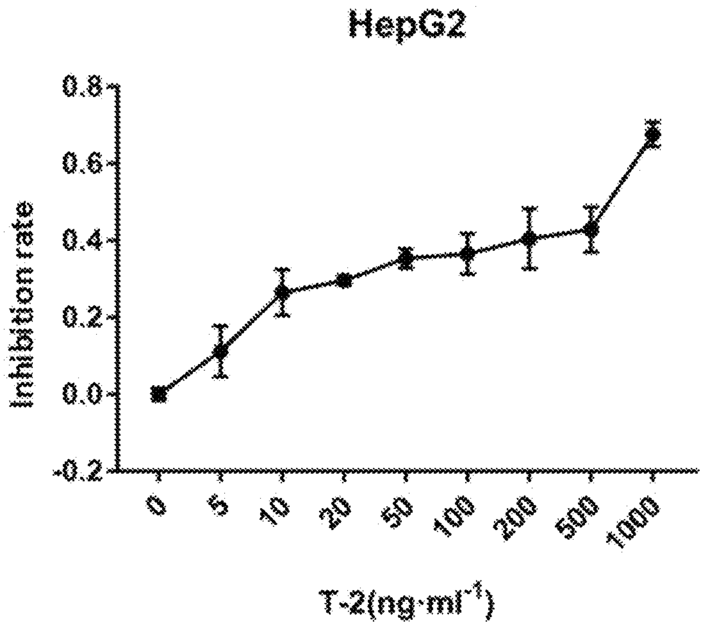
FIG. 5 shows experimental results in evaluation of the cell proliferation activity by a CCK8 method.

From FIG. 5, the single-cell-based electrochemical sensor constructed in Example 1 for evaluating the cytotoxicity of T-2 toxins is in good agreement with the results measured by traditional cytotoxicity methods, and can effectively determine the cytotoxicity of the toxins.

Determination of the levels of intracellular reactive oxygen species (ROS): The levels of reactive oxygen species in vivo after cells were stimulated by fungal toxins are detected by a DCFH-DA fluorescent probe. HepG2 cells were inoculated into six-well plates. After the cells adhered and entered a logarithmic growth phase, complete culture media containing T-2 toxins of different concentrations were added, and the cells were incubated in a carbon dioxide incubator for 24 h. The culture media were discarded, and the cells were washed by centrifugation with PBS, and suspended by blowing. DCFH-DA with a final concentration of 10 μmol/L was added and mixed well for incubation at 37° C. for 30 min in the dark to promote full binding of a probe to the cells. Finally, the cells were washed twice with a serum-free MEM culture medium, the average fluorescence intensity (at an excitation wavelength of 488 nm, and an emission wavelength of 530 nm) was measured by a microplate reader, and fluorescence pictures were taken by an inverted fluorescence microscope.

Figure 6A:
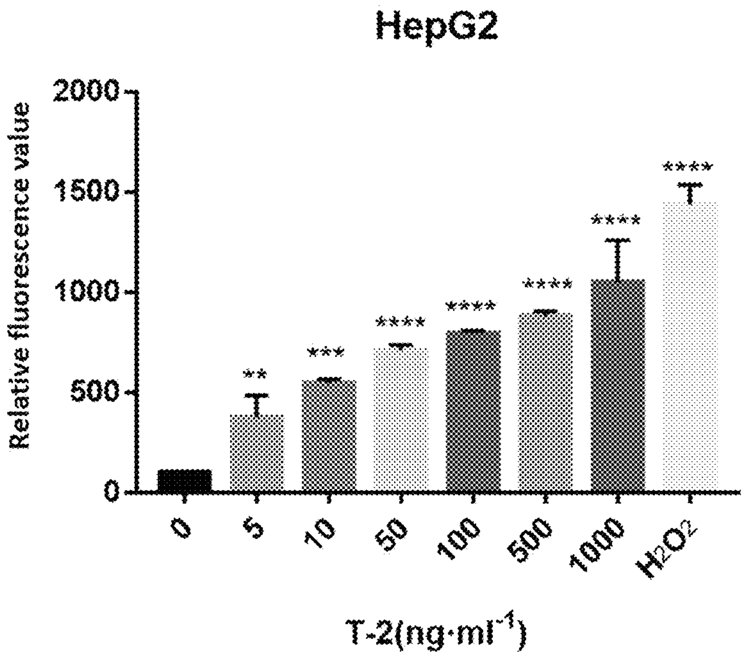
FIG. 6A shows experimental results in evaluation of intracellular reactive oxygen species by a DCFH-DA fluorescence method in Example 3: fluorescence intensities obtained by determination of reactive oxygen species in HepG2 cells.
Figure 6B:
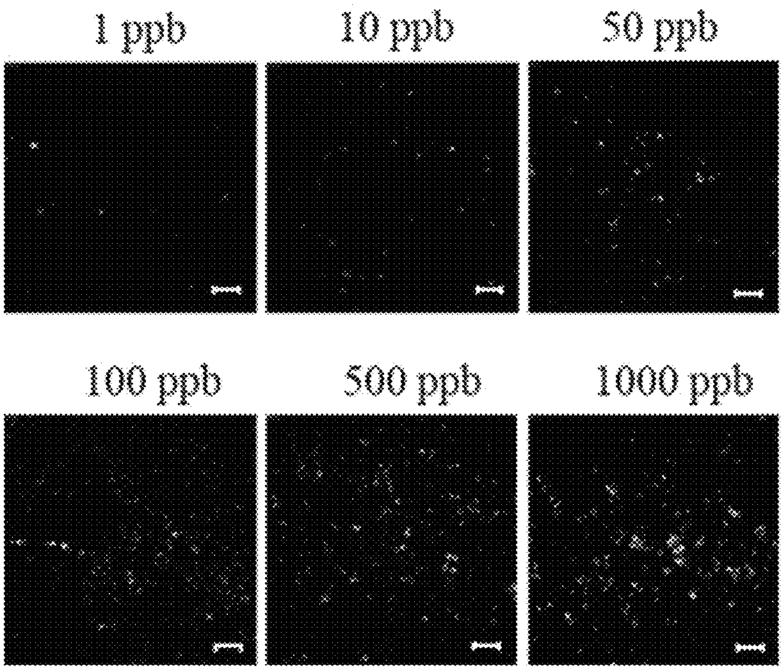
FIG. 6B shows fluorescence images of the reactive oxygen species in the HepG2 cells.

From FIG. 6A and FIG. 6B, the dose-response relationship determined by the single-cell-based electrochemical sensor constructed in Example 1 is in good agreement with the fluorometric assay values of ROS, and the cytotoxicity of the toxins can be effectively determined.

Example 4 Real-Time Monitoring by Single-Cell-Based Electrochemical Sensing

Figure 7:
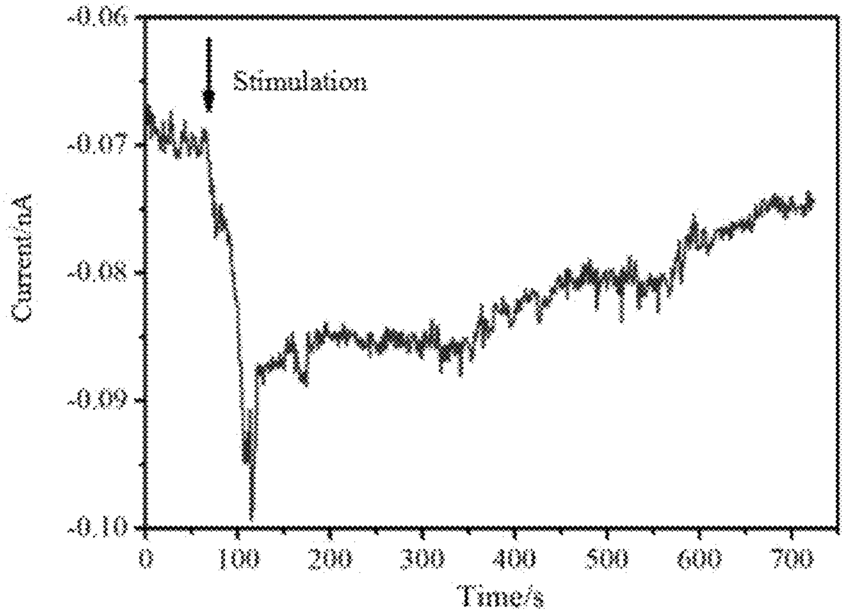
FIG. 7 shows a real-time chronoamperogram of a HepG2 single cell stimulated by 1 ppb T-2 toxin (a nano-probe penetrates the single cell at 0 s, and the T-2 toxin is added to a culture dish at 60 seconds).

Electrochemical sensors can easily quantify targets and further analyze real-time data for key parameters of a biochemical process. To achieve real-time monitoring of the biochemical process of a cell, a nano-probe was brought into contact with the cytoplasm and 1 ppb of T-2 toxin was added to a culture dish. FIG. 7 indicates that real-time current traces of $H_2O_2$ in a single HepG2 cell were detected by single-cell-based electrochemical sensing after T-2 toxin stimulation. When the T-2 toxin was added to the culture dish for stimulation within approximate 60 s, the current value increased 20 s after stimulation. Compared with a control group, the experimental group showed a clear peak current at about 70 s after stimulation. When the peak current was reached, the current stabilized for 1-5 min and then gradually decreased. A redox equilibrium of cells was controlled by balancing ROS production and eliminating ROS through an ROS scavenging system.

Comparative Example 1

Figure 8A:
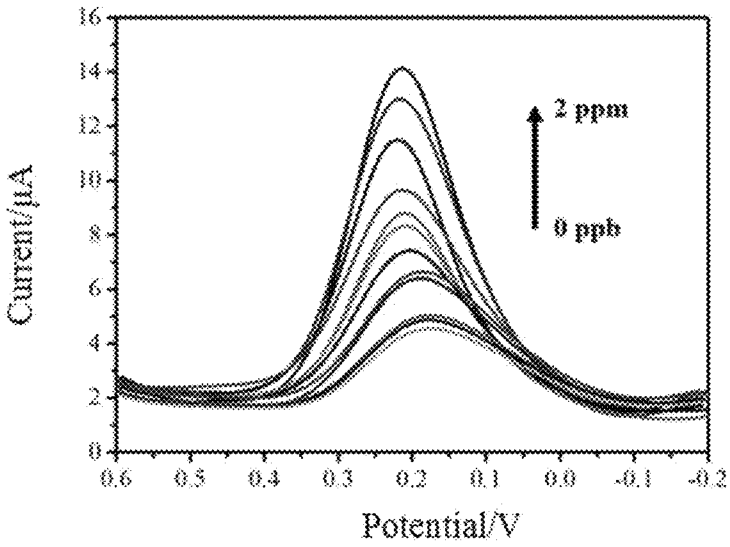
FIG. 8A shows DPV curves of a HepG2 cell stimulated with T-2 toxin detected by GelMA/AuNPs/GCE cell-based electrochemical sensing, and the concentrations of the T-2 toxin from bottom to top are 0 ppb, 1 ppb, 2 ppb, 5 ppb, 10 ppb, 20 ppb, 100 ppb, 200 ppb, 500 ppb, 1 ppm, and 2 ppm.
Figure 8B:
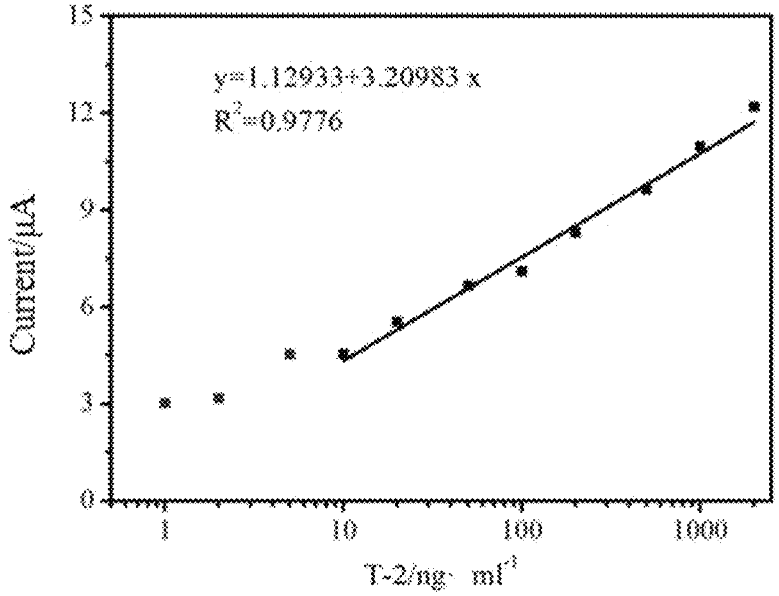
FIG. 8B shows linear fitting of peak currents of T-2 toxin-stimulated cells detected by the GelMA/AuNPs/GCE multicell-based electrochemical sensor.

The single-cell-based electrochemical sensing of Example 1 was adjusted to multicell-based electrochemical sensing:

A cleaned and polished glassy carbon electrode (GCE) was immersed in a 0.5 M $H_2SO_4$ solution containing 1 mM of $HAuCl_4$ and electrodeposited by potential-controlled coulometry (at a potential of −0.25 V for 100 s). The modified electrode was placed in an electrolyte for CV scanning at a cycling voltage of −0.6 V to 0.6 V, and a scanning speed of 0.1 V/s. A digested cell suspension was mixed with a gelatin-methacryloyl (GelMA) hydrogel to ensure a concentration of $10^6$ cells/mL. 6 μL of the mixture was then added to an electrode surface. After photofixation, stimulation with T-2 toxins of different concentrations was conducted for 8 h and electrochemical detection of GelMA/AuNP/GCE was conducted (FIG. 8A). Peak currents were linearly fitted (FIG. 8B). The T-2 toxin concentration had a good linear relationship with the peak current in the range of 10 ppb-1 ppm, $R^2$=0.9776, and the lowest detection concentration was 10 ng/mL.

The results show that, compared with the traditional multicell-based electrochemical detection using the glassy carbon electrode, single-cell-based electrochemical detection is more convenient, efficient and sensitive for T-2 toxin detection.

Example 5 Effect of Gold Deposition Process on Sensor

Referring to Example 1, a gold deposition process was replaced as follows: the gold deposition time was optimized, and nano-probes were immersed in a solution containing 1 $mmol{\cdot}L^{-1}$ chloroauric acid and 0.5 $mol{\cdot}L^{-1}$ sulfuric acid, and electrodeposited at an initial potential of −0.25V for 5 s, 10 s, 15 s, 20 s, 25 s, and 30 s, respectively. Electrical signals of the gold-coated electrodes were detected by DPV, and changes in cell morphology were observed by penetrating the cells with the nano-probes.

With other conditions remained unchanged, the corresponding functionalized nano-probes were prepared.

Figure 9:
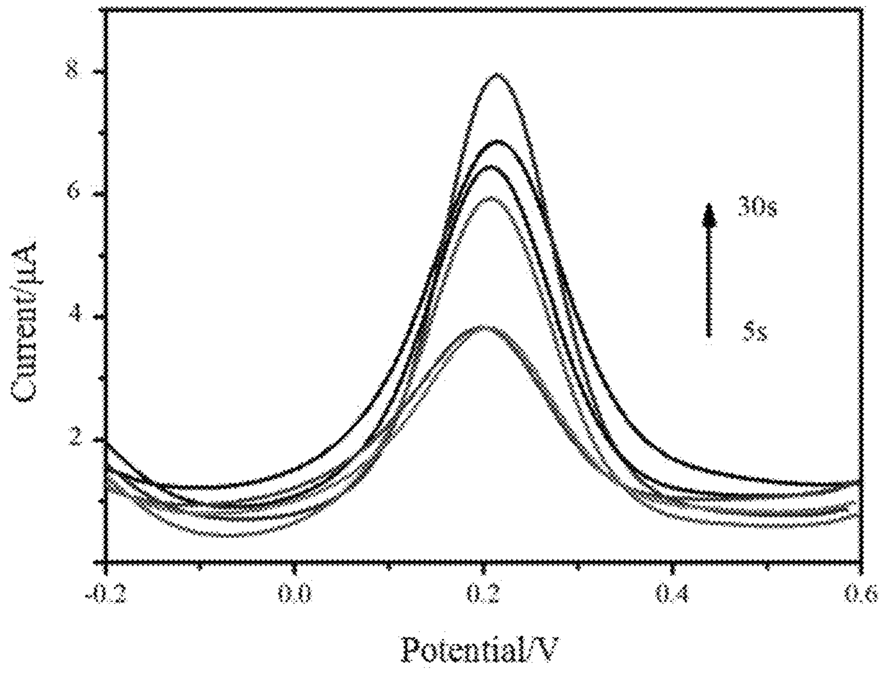
FIG. 9 shows DVP curves of the effects of different gold plating times on nano-probe signals.

Referring to Example 2, as shown in FIG. 9, the longer the gold plating time, the greater the peak current displayed by DPV. However, when the gold-plated nano-probes were penetrated into cells, the nano-probes plated for 25 s and 30 s had obvious damage to the cells, and the cells had obvious depressions after penetration, indicating that the gold-plating time was too long and the diameters of the probes were too large, so the preferred gold-plating time is 20 s.

Example 6 Effect of Prussian Blue Deposition Process on Sensor

Referring to Example 1, a Prussian blue deposition process was replaced as follows: the Prussian blue deposition cycle was optimized, and nano-probes were further modified with Prussian blue by electrochemical deposition in a plating solution containing 0.1 M of HCl, 2 mM of $FeCl_3$, 0.1 of M KCl, and 2 mM of $K_3[Fe(CN)_6]$ at a potential of 0.2 V to −0.6 V for 10 cycles, 20 cycles, 50 cycles, 100 cycles, and 150 cycles respectively. 20 μM of $H_2O_2$ was detected by chronoamperometry.

With other conditions remained unchanged, the corresponding functionalized nano-probes were prepared.

Figure 10:
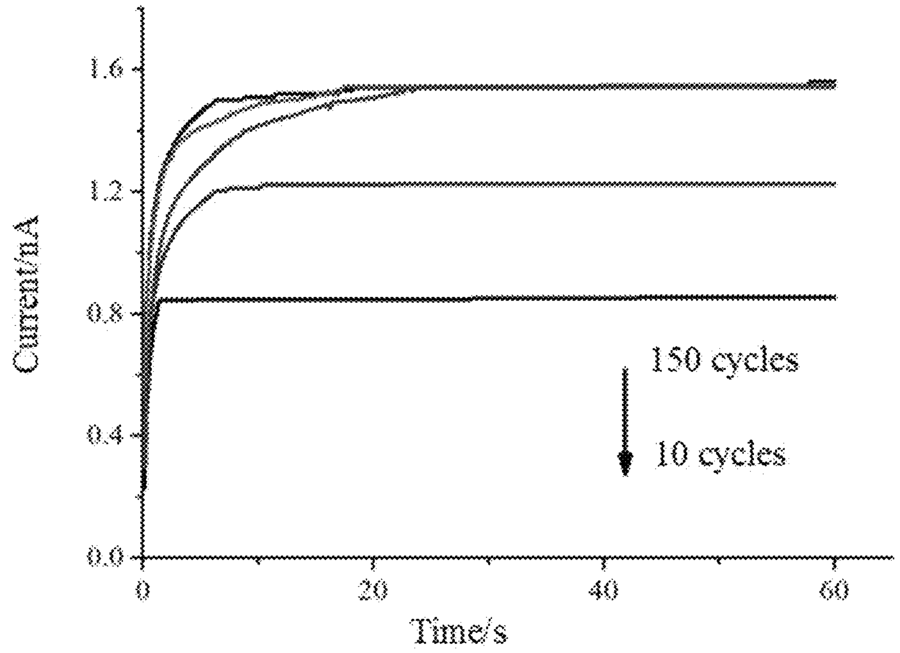
FIG. 10 shows chronoamperometry curves of the effects of modification of Prussian blue for different cycles on the nano-probe.

Referring to Example 2, as shown in FIG. 10, the more the cycles, the greater the measured current value of hydrogen peroxide, and when 50 cycles or more were reached, the current value tended to be stable, so 50 cycles were selected as a Prussian blue modification condition.

What is claimed is:

1. A method for detecting cytotoxicity of T-2 toxins by single-cell-based electrochemical sensor, wherein the method comprises:

diluting a toxin standard substance with a culture medium into a set of solutions making up a gradient of concentrations, incubating the set of solutions in cell culture dishes, preparing the single-cell-based electrochemical sensor, and conducting electrochemical detection by contacting the single-cell-based electrochemical sensor to the set of solutions in the cell culture dishes, and analyzing the cytotoxicity of the toxins by electrochemical chronoamperometry;

wherein preparing the single-cell-based electrochemical sensor comprises:

pulling a capillary into a nano-microneedle, wherein the nano-microneedle comprises a microneedle tip, depositing gold nanoparticles on the microneedle tip to prepare a nano-probe, and depositing Prussian blue on the nano-probe to obtain the single-cell-based electrochemical sensor which is also a functionalized nano-probe.

2. The method of claim 1, wherein the depositing gold nanoparticles comprises: immersing the microneedle tip in a sulfuric acid solution comprising chloroauric acid at an initial potential of −0.25 V for 15-20 s.

3. The method of claim 2, wherein a concentration of chloroauric acid in the sulfuric acid solution is 1 $mmol{\cdot}L^{-1}$, and a concentration of sulfuric acid is 0.5 $mol{\cdot}L^{-1}$.

4. The method of claim 1, wherein the depositing Prussian blue comprises: conducting electrochemical deposition in a plating solution containing 0.1 M HCl, 2 mM $FeCl_3$, 0.1 M KCl, and 2 mM $K_3[Fe(CN)_6]$, at a potential of 0.2 V to −0.6 V for 50 cycles.

5. The method of claim 1, wherein preparing the single-cell-based electrochemical sensor further comprises:

pulling the glass capillary into the nano-microneedle with a micropipette puller, depositing the gold nanoparticles on to the microneedle tip by electrodeposition thereby forming a gold nanoparticle layer on the microneedle tip, providing an electrode comprising an outer layer that is insulated with PDMS, wrapping the microneedle tip of the functionalized nano-probe with Apiezon wax, and exposing the gold nanoparticle layer at the microneedle tip to function as an electrochemical sensing part;

depositing Prussian blue on the functionalized nano-probe by electrochemical deposition, thereby forming a Prussian blue-modified functionalized nano-probe, cycling a potential for the electrochemical deposition 50 times, rinsing the Prussian blue-modified functionalized nano-probe with deionized water, and drying the Prussian blue-modified functionalized nano-probe at room temperature.

6. The method of claim 1, wherein analyzing the cytotoxicity of the toxins by electrochemical chronoamperometry further comprises:

constructing standard curve A by testing concentration values of $H_2O_2$ in $H_2O_2$ standard samples and measuring current values output by the single-cell-based electrochemical sensor;

constructing standard curve B by testing concentration values of the set of the toxin standard samples and measuring concentration values of $H_2O_2$; and measuring concentrations of the toxins in samples to be tested by detecting current values in the samples to be tested, and consulting the standard curves A and B to determine the concentrations of toxins in the samples to be tested;

wherein a working electrode of the single-cell-based electrochemical sensor is the functionalized nano-probe prepared by pulling the capillary into the nano-microneedle, and gold nanoparticles are deposited on a microneedle tip to prepare the nano-probe, and then depositing Prussian blue on the microneedle tip to obtain the functionalized nano-probe;

wherein depositing gold nanoparticles comprises: immersing the microneedle tip in a sulfuric acid solution containing chloroauric acid at an initial potential of −0.25 V for 15-20 s; and wherein the process of Prussian blue deposition comprises: conducting electrochemical deposition in a plating solution comprising 0.1 M HCl, 2 mM $FeCl_3$, 0.1 M KCl, and 2 mM $K_3[Fe(CN)_6]$, at a potential of 0.2 V to −0.6 V for 50 cycles.

7. The method of claim 1, wherein analyzing the cytotoxicity of the toxins by electrochemical chronoamperometry comprises:

constructing standard curve A by testing concentration values of $H_2O_2$ in $H_2O_2$ standard samples and measuring current values output by the single-cell-based electrochemical sensor;

constructing standard curve B by testing concentration values of the set of toxin standard samples and measuring concentration values of $H_2O_2$; and measuring concentrations of the toxins in samples to be tested by detecting current values in the samples to be tested, and consulting the standard curves A and B to determine the concentrations of toxins in the samples to be tested.

* * * * *